(12) United States Patent
Yoneda et al.

(10) Patent No.: US 8,630,823 B2
(45) Date of Patent: Jan. 14, 2014

(54) FEATURE PARAMETER CANDIDATE GENERATION APPARATUS AND FEATURE PARAMETER CANDIDATE GENERATION METHOD

(75) Inventors: Mitsuhiro Yoneda, Kyoto (JP); Hiroshi Nakajima, Kyoyo (JP); Naoki Tsuchiya, Kyoto (JP); Hiroshi Tasaki, Kyoto (JP)

(73) Assignee: Omron Corporation, Kyoto (JP)

( * ) Notice: Subject to any disclaimer, the term of this patent is extended or adjusted under 35 U.S.C. 154(b) by 921 days.

(21) Appl. No.: 12/740,336

(22) PCT Filed: Oct. 31, 2008

(86) PCT No.: PCT/JP2008/069951
§ 371 (c)(1),
(2), (4) Date: Apr. 28, 2010

(87) PCT Pub. No.: WO2009/057778
PCT Pub. Date: May 7, 2009

(65) Prior Publication Data
US 2010/0235151 A1    Sep. 16, 2010

(30) Foreign Application Priority Data

Nov. 1, 2007   (JP) ................................ 2007-285178

(51) Int. Cl.
*G06F 7/60* (2006.01)
*G06F 17/10* (2006.01)

(52) U.S. Cl.
USPC ............................................. 703/2; 707/776

(58) Field of Classification Search
CPC .................................................. G06F 17/5018
USPC ...................... 703/2; 707/776, 802, 803, 804
See application file for complete search history.

(56) References Cited

U.S. PATENT DOCUMENTS

| 6,496,834 B1* | 12/2002 | Cereghini et al. | 707/737 |
| 2003/0212678 A1* | 11/2003 | Bloom et al. | 707/6 |
| 2003/0212692 A1* | 11/2003 | Campos et al. | 707/100 |

FOREIGN PATENT DOCUMENTS

| JP | 04-084277 | 3/1992 |
| JP | 9-081731 | 3/1997 |
| JP | 11-126212 | 5/1999 |

* cited by examiner

*Primary Examiner* — Kamini S Shah
*Assistant Examiner* — Luke Osborne
(74) *Attorney, Agent, or Firm* — Foley & Lardner LLP (57) ABSTRACT

A feature parameter candidate generation apparatus has a storage unit that stores the values of feature parameters extracted from each of samples, an index value calculation unit that calculates an index value, which is obtained by normalizing the number of the kinds of the values of feature parameters by the number of the samples, for each of the feature parameters, an evaluation object selection unit that selects combinations of feature parameters which are objects to be evaluated, an evaluation unit that evaluates whether the uniformity of a frequency distribution of index values of the individual feature parameters for combinations of feature parameters selected as the objects to be evaluated satisfies a predetermined criterion, and a candidate determination unit that determines, as feature parameter candidates to be given to the model generation device, a combination of feature parameters that is evaluated to satisfy the predetermined criterion.

7 Claims, 9 Drawing Sheets

| FEATURE PARAM. | REGRESSION COEFFICIENT (AVERAGE ± STANDARD DEVIATION) | | |
|---|---|---|---|
| | METHOD 1 | METHOD 2 | METHOD 3 |
| $a$ | --- | 58.42±11.28 | 60.17±12.41 |
| $b$ | --- | -590±339 | -590±430 |
| $a^2$ | --- | -0.91±0.18 | -0.94±0.21 |
| $b^2$ | --- | 8.07±4.20 | 8.12±5.35 |
| $1/b$ | --- | -217206±131516 | -214590±167130 |
| $1/b^2$ | --- | 1052746±631218 | 1026874+807214 |
| $w^2$ | 0.02±0.04 | --- | --- |
| $1/Z$ | -299±217 | -558.3±167.2 | -618.0±222 |
| $X \cdot w$ | -0.06±0.02 | --- | --- |
| $X(a^2+b^2)^{1/2}$ | --- | -0.075±0.021 | -0.12±0.04 |
| $A$ | --- | 0.74±0.22 | --- |
| $S$ | --- | 11.25±5.65 | --- |

FEATURE PARAMETER CANDIDATE GENERATION APPARATUS AND FEATURE PARAMETER CANDIDATE GENERATION METHOD

TECHNICAL FIELD

The present invention relates to a technique for preparing a feature parameter used as the foundation for modeling.

BACKGROUND ART

In order to prevent diseases and to maintain and improve health, it is necessary to grasp human health conditions (whether the body temperature, blood pressure, body fat, and so on, are in normal ranges, respectively). However, it is difficult to directly measure the health conditions, so in various kinds of health equipment, a model is built which serves to estimate human health conditions based on certain biological information obtained by measurements. For example, in an electronic thermometer, a model is built which estimates body temperature from a temperature measured at underarm. Also, in a sphygmomanometer, a model is built which estimates blood pressure from a pressure applied to an arm and a measured sound. In addition, in a body composition meter, a model is built which estimates body composition such as a body fat ratio, etc., from weight, height, age, sex, and body impedance.

Such kinds of models are generally expressed by estimate equations which take as variates a variety of kinds of feature parameters obtained from humans. At the time of building a model, (1) data are first measured and collected from a lot of subjects being tested, so that feature parameters are prepared. The feature parameters include measured values which are obtained by measurements, calculated values which are calculated from one or a plurality of measured values, attribute values of the subjects being tested such as sex, etc. Then, subsequently, (2) feature parameters used for building a model are selected from the feature parameters thus prepared, and (3) a model is built by using the feature parameters thus selected.

With respect to (2) the selection of a feature parameter and (3) the building of a model, a variety of techniques have been studied and proposed in the past. As existing techniques in relation to (2), there are, for example, a technique that eliminates feature parameters with high similarity in meaning between feature parameters, and high similarity in the way of dividing information by the feature parameters (see patent document 1), a technique that evaluates information content or volume by using average mutual information in a plurality of feature parameters (see patent document 2), a technique that evaluates the goodness of a combination of feature parameters by using an error of prediction (see patent document 3), and so on. In addition, as existing techniques in relation to (3), there are a linear model (a single regression model, a multiple regression model), a non-linear model (a neural network, an SVM (Support Vector Machine)), and so on.

Patent Document 1: Japanese patent application laid-open No. 11-126212
Patent Document 2: Japanese patent application laid-open No. 4-84277
Patent Document 3: Japanese patent application laid-open No. 9-81731

DISCLOSURE OF THE INVENTION

Problems to be Solved by the Invention

A human (living body) has special structural properties or characterizations of "complexity" and "individuality". The complexity of a living body means that the living body is composed of various elements such as muscles, bones, fats, and so on, and the individuality of a living body means that a variation due to individual differences or specificities exists in the characteristic of each of the elements which constitute the living body. Thus, because of the presence of the complexity and individuality of the living body, the information measured from the living body becomes a compound quantity affected by the influence of variations in various component elements in the living body. Besides, it is considered that the variations contained in the information include variations of different characteristics, i.e., variations which are involved in an estimation object to be targeted (e.g., a body fat ratio), and variations which are not involved therein. A modeling in consideration of the characteristics of such variations is extremely difficult.

With reference to such problems, the present inventors have obtained an idea that modeling with high accuracy and high reliability can be made possible by securing, in a preparatory step of feature parameters in (1) above, variations of the feature parameters so that each character or property for the complexity and individuality may be covered. That feature parameters with different properties, such as feature parameters which react sensitively to variations due to the complexity and/or individuality of the living body, and feature parameters which can not be easily affected by the influence of variations due to the complexity and/or individuality of the living body, are prepared in an exhaustive manner.

However, in the past, there has been no effective technique of evaluating the property of a feature parameter in a quantitative manner, so there has been no other choice than to take an inefficient technique of preparing a feature parameter through trial and error based on prior knowledge about the object to be predicted.

The present invention has been made in view of the abovementioned actual circumstances, and has for its object to provide a technique that makes it possible to efficiently prepare candidates for feature parameters with different properties, which become particularly effective in modeling an object with complexity and individuality.

Means for Solving the Problems

In order to achieve the above-mentioned object, the present invention adopts the following construction.

The present invention resides in a feature parameter candidate generation apparatus for generating feature parameter candidates to be given to a model generation device that builds a model by using a plurality of feature parameters selected from given feature parameter candidates, the feature parameter candidate generation apparatus comprising: a storage unit that stores the values of a plurality of kinds of feature parameters extracted from each of a plurality of samples; an index value calculation unit that calculates an index value, which is obtained by normalizing the number of the kinds of the values of the feature parameters by the number of the samples, for each of the plurality of kinds of feature parameters; an evaluation object selection unit that selects, from the plurality of kinds of feature parameters, combinations of feature parameters which are objects to be evaluated, an evaluation unit that evaluates whether the uniformity of a frequency distribution of index values of the individual feature parameters for the combinations of feature parameters selected as the objects to be evaluated satisfies a predetermined criterion; and a candidate determination unit that determines, as feature parameter candidates to be given to the model generation device, a combination of feature parameters that is evaluated to satisfy the predetermined criterion by the evaluation unit.

In the present invention, the property of each feature parameter is quantified by using "an index value that is obtained by normalizing the number of the kinds of the values of the feature parameters by the number of the samples". Then, candidates of feature parameters are selected so that a frequency distribution of index values thereof becomes uniform to a certain extent. By doing so, feature parameters of various properties will be exhaustively arranged in a well-balanced manner as feature parameter candidates. Then, by building a model based on such feature parameter candidates, it is possible to expect improvements in the accuracy and performance of the model.

In the present invention, it is preferable to repeat an update of an object to be evaluated by the evaluation object selection unit and an evaluation of the updated object to be evaluated by the evaluation unit so as to find out a combination of feature parameters which satisfies the predetermined criterion.

By executing such search processing, it is possible to select an optimal or suitable combination of feature parameters from many feature parameters in an automatic manner. As for a specific technique of the search processing, a round robin may be used, or an existing search algorithm may be applied.

For example, the evaluation object selection unit may update the objects to be evaluated by adding, among the plurality of kinds of feature parameters, a feature parameter which is not included in the objects to be evaluated to the objects to be evaluated. At this time, the evaluation object selection unit may specify a portion which indicates a minimum frequency in a frequency distribution of index values of feature parameters included in the objects to be evaluated, and select, as a feature parameter added to the objects to be evaluated; a feature parameter which has an index value corresponding to the portion indicating the minimum frequency.

By doing so, a feature parameter suitable to improve the uniformity of the frequency distribution is selected as an object to be added, so an increase in efficiency of the search processing can be attained, and a suitable feature parameter candidate can be determined in a quicker manner.

In addition, the evaluation object selection unit may update the objects to be evaluated by changing the resolution of the values of at least any feature parameter among feature parameters included in the objects to be evaluated. At this time, the evaluation object selection unit may specify a portion which indicates a maximum frequency in a frequency distribution of index values of feature parameters included in the objects to be evaluated, and change the resolution of a feature parameter which has an index value corresponding to the portion indicating the maximum frequency.

If the resolution of the values of a feature parameter is made coarser, an index value thereof will become smaller, and if the resolution is made finer, an index value will become larger. Thus, by changing the resolution of a feature parameter which has an index value corresponding to that portion which indicates a maximum frequency thereby to make the index value smaller or larger, it is possible to improve the uniformity of the frequency distribution thereof. This technique is effective in case where the index values of a plurality of kinds of feature parameters stored in the storage unit are unevenly distributed, or in case where a feature parameter with an index value corresponding to a portion with a small frequency does not exist in the storage unit, or in the like cases.

The present invention may be regarded as a feature parameter candidate generation apparatus which includes at least a part of the above-mentioned units, or may be regarded as a modeling system which is provided with the above-mentioned feature parameter candidate generation apparatus and the above-mentioned model generation device. In addition, the present invention can also be regarded as a feature parameter candidate generation method which includes at least a part of the above-mentioned processes, or a program for achieving such a method, or a computer readable recording medium which has such a program recorded thereon. Here, note that each of the above-mentioned units and processes can be combined with one another as much as possible so as to achieve the present invention.

For example, a feature parameter candidate generation method according to the present invention resides in a feature parameter candidate generation method for generating feature parameter candidates to be given to a model generation device that builds a model by using a plurality of feature parameters selected from given feature parameter candidates, the feature parameter candidate generation method being characterized in that a computer, which is provided with a storage unit that stores the values of a plurality of kinds of feature parameters extracted from each of a plurality of samples, executes: an index value calculation step that calculates an index value, which is obtained by normalizing the number of the kinds of the values of the feature parameters by the number of the samples, for each of the plurality of kinds of feature parameters; an evaluation object selection step that selects, from the plurality of kinds of feature parameters, combinations of feature parameters which are objects to be evaluated; an evaluation step that evaluates whether the uniformity of a frequency distribution of index values of the individual feature parameters for the combinations of feature parameters selected as the objects to be evaluated satisfies a predetermined criterion; and a candidate determination step that determines, as feature parameter candidates to be given to the model generation device, a combination of feature parameters that is evaluated to satisfy the predetermined criterion by the evaluation step.

In addition, a feature parameter candidate generation program according to the present invention resides in a feature parameter candidate generation program for generating feature parameter candidates to be given to a model generation device that builds a model by using a plurality of feature parameters selected from given feature parameter candidates, the feature parameter candidate generation program being characterized by causing a computer, which is provided with a storage unit that stores the values of a plurality of kinds of feature parameters extracted from each of a plurality of samples, to execute: an index value calculation step that calculates an index value, which is obtained by normalizing the number of the kinds of the values of the feature parameters by the number of the samples, for each of the plurality of kinds of feature parameters; an evaluation object selection step that selects, from the plurality of kinds of feature parameters, combinations of feature parameters which are objects to be evaluated; an evaluation step that evaluates whether the uniformity of a frequency distribution of index values of the individual feature parameters for the combinations of feature parameters selected as the objects to be evaluated satisfies a predetermined criterion; and a candidate determination step that determines, as feature parameter candidates to be given to the model generation device, a combination of feature parameters that is evaluated to satisfy the predetermined criterion by the evaluation step.

Effect of the Invention

According to the present invention, it is possible to efficiently prepare candidates for feature parameters with different properties, which become effective in modeling an object with complexity and individuality.

BEST MODE FOR CARRYING OUT THE INVENTION

Hereinafter, a preferred embodiment of this invention will be described in detail by way of example with reference to the attached drawings.

<Evaluation Index of Feature Parameter>

In the past, there has been no effective technique for evaluating the property of a feature parameter in a quantitative manner, and hence, even if feature parameters with different properties are to be prepared in an exhaustive manner so as to comply with the complexity and individuality of a living body, there has been no other method than to sharply distinguish and prepare feature parameters by way of trial and error, and such a method has been very inefficient.

Accordingly, in this embodiment, a concept of cardinality (density) is introduced. The cardinality is a concept indicating the number of elements of a set, and is an index indicating a density which feature parameters can have, i.e., the number of the kinds of the values of feature parameters. For example, suppose that the following feature parameters were obtained from five subjects or persons being tested.

(1) Sex: man, height: 170 cm, weight: 59 kg
(2) Sex: man, height: 173 cm, weight: 65 kg
(3) Sex: man, height: 168 cm, weight: 65 kg
(4) Sex: woman, height: 152 cm, weight: 42 kg
(5) Sex: woman, height: 159 cm, weight: 50 kg In this sample, elements for a feature parameter "sex" are a "man" and a "woman", and its cardinality becomes "2". In addition, the cardinality of a feature parameter "height" is "5", and the cardinality of "weight" is "4". By using this concept of cardinality, the expression ability of each feature parameter with respect to a variation can be quantified.

However, there is a problem that the value of this cardinality is affected by the influence of the scale of the set, i.e., the number of sample data. For example, in the case of a feature parameter, such as "height", having a high possibility that its value changes with individuals, the value of the cardinality thereof also becomes larger in accordance with the increasing number of the sample data. As a consequence, in this embodiment, an evaluation index called NC (Normalized Cardinality) is defined which is obtained by normalizing the cardinality by the number of samples, as shown in the following equation. The domain (range of values) of the NC becomes $0 < NC \leq 1$, as is clear from the following equation.

$$NC = (\text{cardinality})/(\text{number of sample data})$$

A feature parameter with a small normalization cardinality NC can also be said to have a property which is less prone to be affected by the influence of a variation due to the complexity and/or the individuality of the living body. If such a feature parameter is incorporated in a model, there can be expected an effect that errors resulting from the variation due to the complexity and the individuality of the living body can be absorbed, thereby improving the stability of the model.

On the other hand, a feature parameter with a large normalization cardinality NC can be said to have a property which is able to express a variation due to the complexity and/or the individuality of the living body with high accuracy. If such a feature parameter is incorporated in a model, there can be expected an effect that the accuracy and the power of expression of the model are enhanced.

Accordingly, in order to build a model with high reliability which combines both stability and accuracy, it can be said that it is desirable to use both a feature parameter with a large normalization cardinality NC and a feature parameter with a small normalization cardinality NC. As a consequence, in a system of this embodiment to be described below, an approach is adopted in which feature parameters with normalization cardinalities NC ranging from a large value to a small value are prepared exhaustively in a well-balanced manner in a preparatory step of the feature parameters. By first preparing such feature parameter candidates, highly reliable modeling resultantly becomes possible in later feature parameter selection processing and/or in later modeling processing.

<System Construction>

Figure 1:
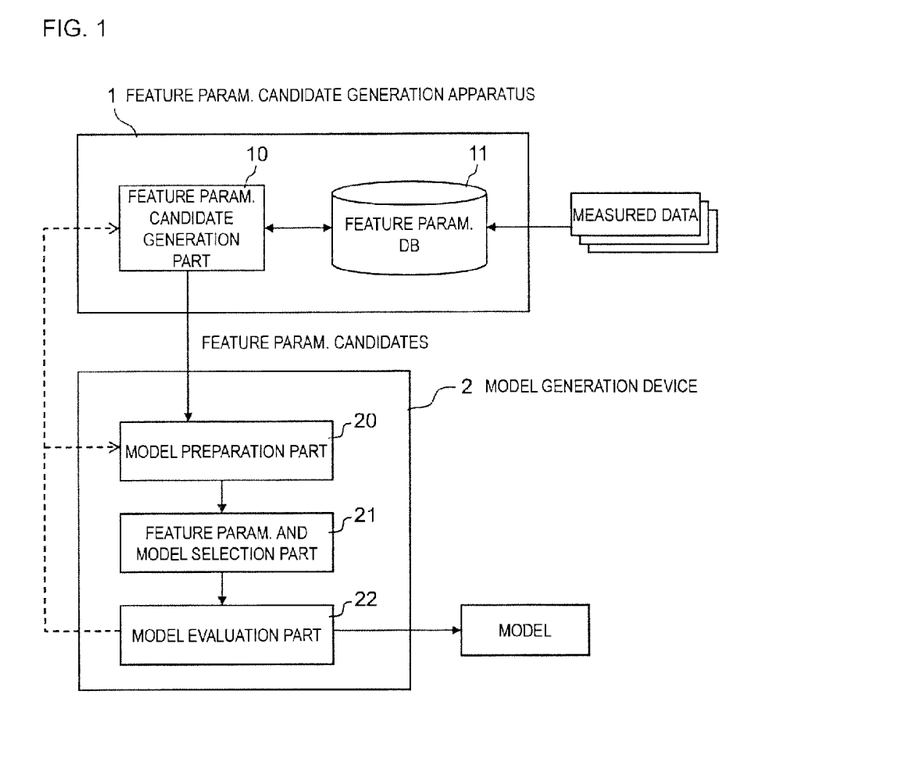
FIG. 1 is a view schematically showing the construction of a modeling system according to an embodiment of the present invention.

FIG. 1 is a view schematically showing the construction of the modeling system according to the embodiment of the present invention.

The modeling system is generally provided with a feature parameter candidate generation apparatus 1 that creates or generates feature parameter candidates based on normalization cardinalities NC, and a model generation device 2 which performs the selection of feature parameters and modeling based on the feature parameter candidates given from the feature parameter candidate generation apparatus 1. The feature parameter candidate generation apparatus 1 is provided with a feature parameter candidate generation part 10 and a feature parameter database 11, and the model generation device 2 is provided with a model preparation part 20, a feature parameter and model selection part 21, and a model evaluation part 22.

This modeling system is a system that generates a model (estimate equation) to be estimated in an automatic manner based on measurement data and attribute data which were obtained from a lot of subjects (samples) being tested. As the object to be estimated, there are assumed, for example, those which indicate the health condition of a human, such as body composition such as body fat percentage and visceral fat amount, body temperature, blood pressure, and so on. As the measurement data, there are used various kinds of information measured from the living body, such as, for example, body height, body weight, circumferential waist size or length, body impedance, temperature, cardiac beats, etc., and as the attribute data, there are used, for example, age, sex, etc. Because the causal relation between the measurement data or attribute data and the object to be estimated is often unknown, it is desirable to collect as many kinds of data as possible. The measurement data and the attribute data collected in advance are stored in the feature parameter database 11.

In terms of hardware, the modeling system can be constructed of a general-purpose computer equipped with a CPU, a memory, an auxiliary storage, a display device, an input device, etc. For the purpose of such construction, only one computer may be used, or a plurality of computers may be used. Thus, the above-mentioned respective functions of the modeling system are achieved by software programs which are stored in the auxiliary storage and are executed by the CPU with the use of hardware resources as necessary.

<Function and Operation>

Figure 2:
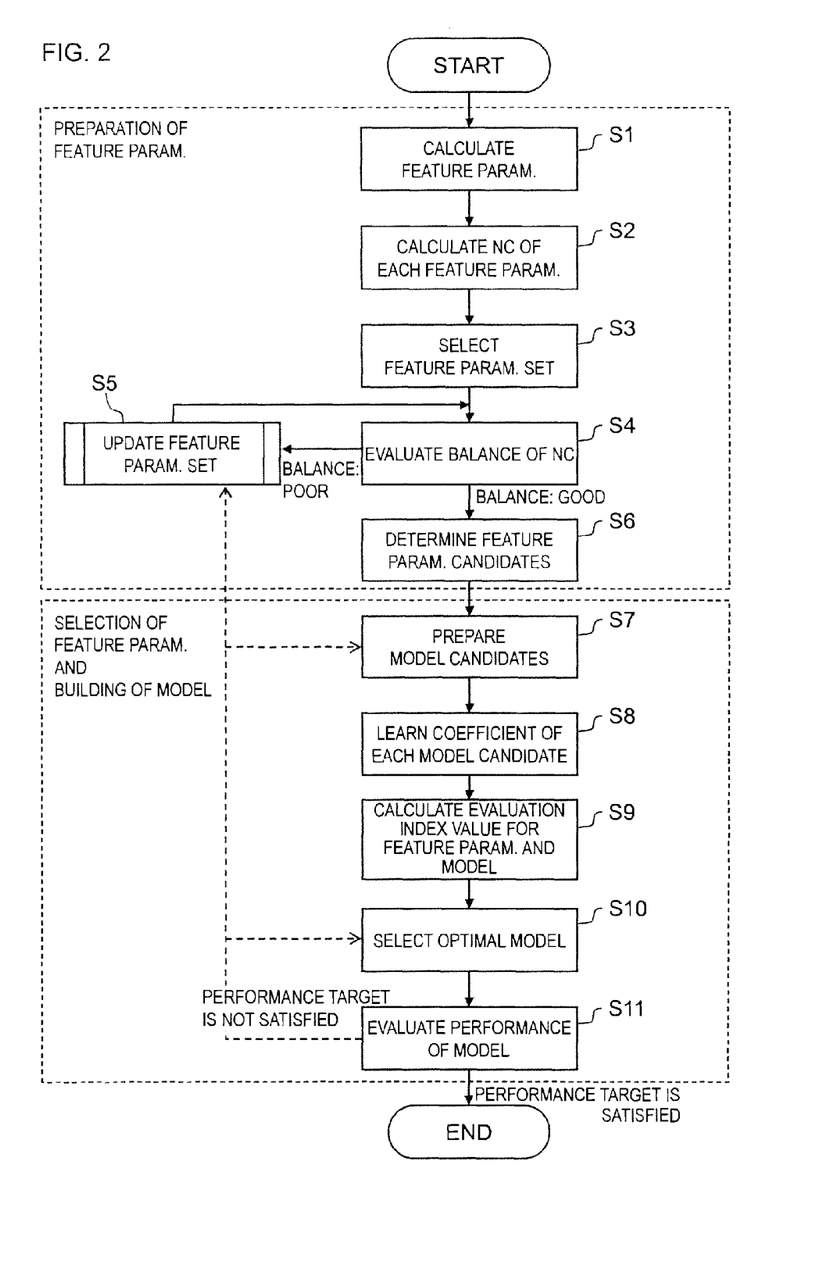
FIG. 2 is a view showing an entire flow of this system.

Next, reference will be made to the function and operation of each part of the modeling system, while referring to a flow chart in FIG. 2. FIG. 2 is a view showing an entire flow of this system.

(Feature Parameter Candidate Generation Apparatus: Preparation of Feature Parameters)

In step S1, the feature parameter candidate generation part 10 reads in measurement data and attribute data from the feature parameter database 11, and calculates feature parameters from those data. Here, the measurement data (measured values) and the attribute data (attribute values) themselves are called primary feature parameters, and a calculated value(s) calculated from one or a plurality of measured values is or are called a secondary feature parameter or quantities. For example, a waist circumferential length w and a body impedance Z measured from a subject or person to be tested are primary feature parameters, and $w^2$, $1/w$, $Z \times w$, etc., which are obtained with their dimensional extension and combination, are secondary feature parameters. What kinds of things are generated as secondary feature parameters may be beforehand set in the feature parameter candidate generation part 10, or a variety of forms of secondary feature parameters may be generated at random or exhaustively.

The feature parameters (including the primary feature parameters and the secondary feature parameters) calculated by the feature parameter candidate generation part 10 are stored in the feature parameter database 11 which serves as a storage unit. According to this, the values of the feature parameters extracted (measured, acquired or calculated) from each of the plurality of samples are prepared, for the plurality of kinds of feature parameters, in the feature parameter database 11. However, these feature parameters are merely collected and calculated in an automatic manner, so things of different properties are not necessarily contained exhaustively in a well-balanced manner, and they may be too numerous if all of them are designated as feature parameter candidates. As a consequence, the feature parameter candidate generation part 10 generates feature parameter candidates in the following steps.

In step S2, the feature parameter candidate generation part 10 calculates the value of normalization cardinality NC for each of the plurality of kinds of feature parameters stored in the feature parameter database 11. Here, note that in this embodiment, this function of the feature parameter candidate generation part 10 corresponds to an index value calculation unit of the present invention.

In step S3, the feature parameter candidate generation part 10 selects from the plurality of kinds of feature parameters a combination of feature parameters (feature parameter set) to be made the objects to be evaluated. An initial feature parameter set may be selected in any manner. For example, such a selection may be made at random, or a combination of feature parameters may be selected which makes the dispersion of the value of NC larger. Here, note that in this embodiment, this function of the feature parameter candidate generation part 10 corresponds to an evaluation object selection unit of the present invention.

In step S4, the feature parameter candidate generation part 10 evaluates the feature parameter set selected in step S3 as an object to be evaluated as to whether the uniformity of the frequency distribution of the normalization cardinalities of respective feature parameters satisfies a predetermined criterion. That is, an evaluation is made as to whether the feature parameters are distributed over an entire range of values of 0-1 in a well-balanced manner in a histogram (hereafter referred to as an NC histogram) in which the axis of abscissa is the value of NC (the value range being 0-1), and the axis of ordinate is the frequency (the number of feature parameters). As such a method of evaluation, there can be used, for example, a Kolmogorov Smirnov test or the like. Here, in cases where the uniformity of the NC histogram is evaluated to satisfy the predetermined criterion (i.e., the balance of NC is good), the flow advances to step S6, whereas in cases where it is evaluated that the predetermined criterion is not satisfied (i.e., the balance of NC is poor), the flow advances to step S5. Here, note that in this embodiment, this function of the feature parameter candidate generation part 10 corresponds to an evaluation unit of the present invention.

In step S5, the feature parameter candidate generation part 10 updates the feature parameter set to be evaluated. As a technique of updating the feature parameter set so that the balance of NC becomes good, either or both of two techniques, "the addition of a feature parameter" and "the adjustment of the resolution of a feature parameter", are used here.

Figure 3:
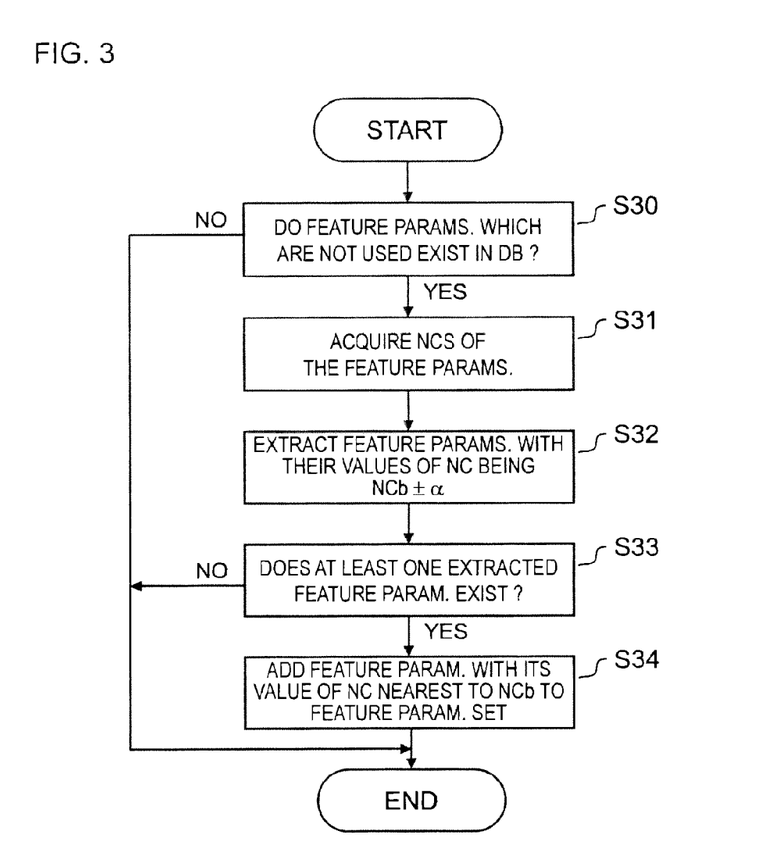
FIG. 3 is a flow chart showing specific processing of adding a feature parameter.
Figure 4:
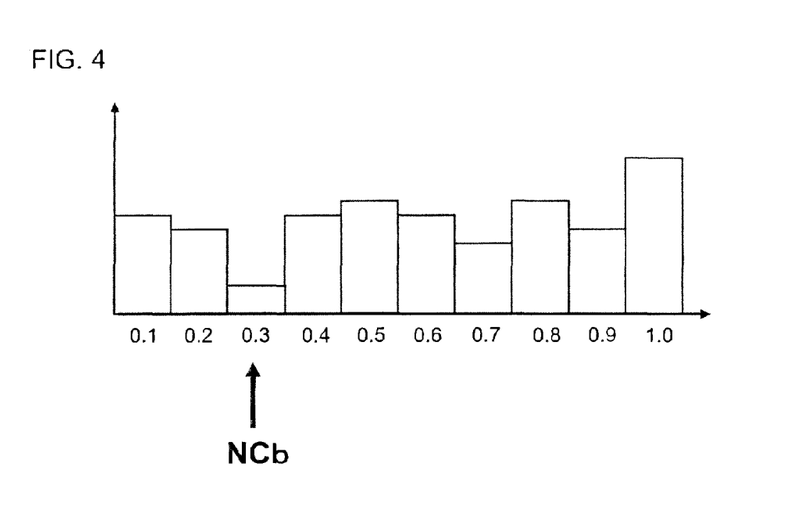
FIG. 4 is an NC histogram for explaining the processing of adding a feature parameter.

FIG. 3 is a flow chart showing specific processing of adding a feature parameter. In step S30, the feature parameter candidate generation part 10 checks whether there exist feature parameters (not contained in the feature parameter set under evaluation) which is not used in the feature parameter database 11. In cases where they exist, the values of the NCs thereof are acquired in step S31. Then, in step S32, the feature parameter candidate generation part 10 specifies a portion which indicates a minimum frequency in the NC histogram of the current objects to be evaluated. For example, if the NC histogram is as shown in FIG. 4, the portion indicating the minimum frequency is a portion of which the value of its NC is 0.3. Hereinafter, the value of the NC of the portion which indicates the minimum frequency is referred to as NCb, and the value of the NC of a portion which indicates a maximum frequency is referred to as NCp. The feature parameter candidate generation part 10 extracts, from the feature parameters obtained in step S30, those feature parameters of which the values of the NCs thereof are included in a range of NCb±α (α is a value which is set beforehand, for example, α=0.05). In cases where there is at least one or more feature parameters extracted here (step S33; YES), then in step S34, a feature parameter with the value of its NC nearest to NCb is added to the feature parameter set which is to be evaluated.

Figure 5:
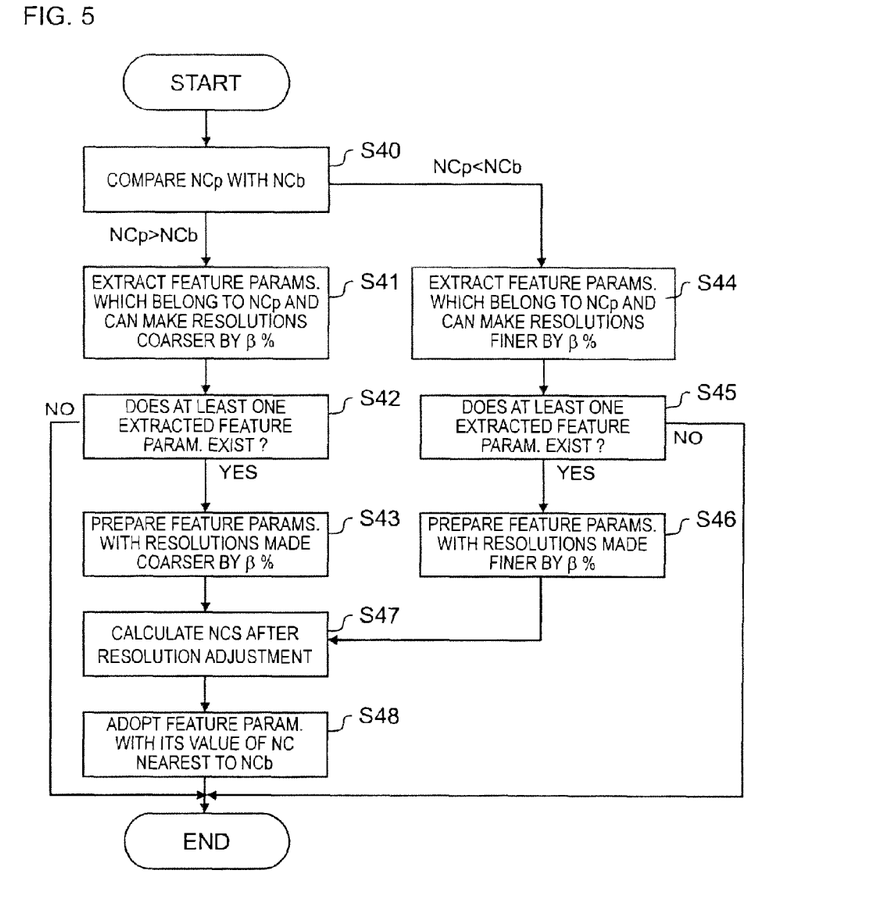
FIG. 5 is a flow chart showing specific processing adjusting the resolution of a feature parameter.

FIG. 5 is a flow chart showing specific processing of adjusting the resolution of a feature parameter. In step S40, the feature parameter candidate generation part 10 makes a comparison between the magnitudes of NCp and NCb in the NC histogram to be currently evaluated.

Figure 6:
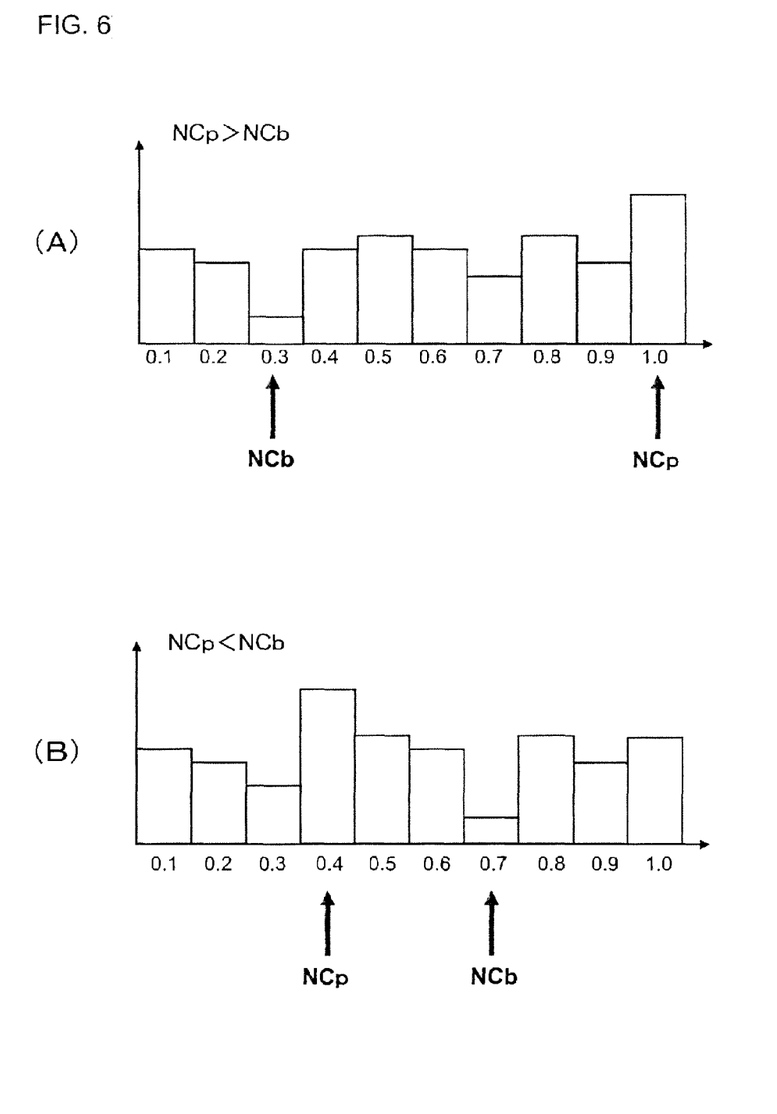
FIG. 6A and FIG. 6B are NC histograms for explaining the processing of adjusting the resolution of a feature parameter.

In the case of NCp>NCb (see FIG. 6A), the flow advances to step S41. In step S41, the feature parameter candidate generation part 10 extracts, among the feature parameters belonging to the portion of NCp, those in which their resolutions can be made coarser by β % (β is a value which is set beforehand, for example, β=50%). Here, to adjust a resolution means to change an increment of values (discrete values) which a feature parameter can take, and to make a resolution coarser means to make an increment larger, and to make a resolution finer means to make an increment smaller. If the value of a feature parameter is given by a real value, its resolution can in principle be adjusted by an arbitrary increment or amount. In cases where there is at least one or more feature parameters extracted in step S41 (step S42; YES), feature parameters in which the resolutions of the feature parameters thus extracted are made coarser by β % are prepared (step S43), and the flow advances to step S47.

On the other hand, in the case of NCp<NCb (see FIG. 6B), the flow advances to step S44. In step S44, the feature parameter candidate generation part 10 extracts, among the feature parameters belonging to the portion of NCp, those in which their resolutions can be made finer by β %. In cases where there is at least one or more feature parameters extracted (step S45; YES), feature parameters in which the resolutions of the feature parameters thus extracted are made finer by β % are prepared (step S46), and the flow advances to step S47.

Figure 7:
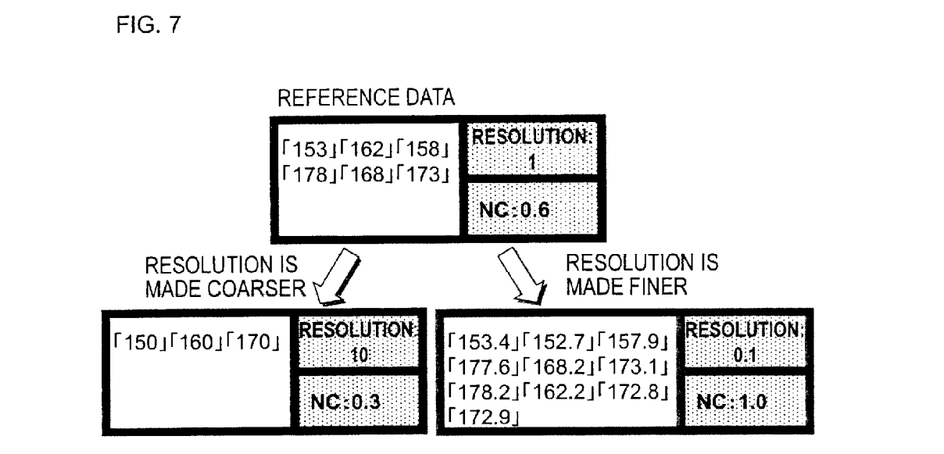
FIG. 7 is a view for explaining the processing of adjusting the resolution of a feature parameter.

In step S47, the feature parameter candidate generation part 10 calculates the NCs of the feature parameters with their resolutions adjusted, which were prepared in step S43 or step S46. As shown in FIG. 7, if the resolution of a feature parameter is made coarser, the number of values which the feature parameter can take will decrease, so the value of the NC thereof becomes smaller. On the contrary, if the resolution of a feature parameter is made finer, the number of values which the feature parameter can take will increase, so the value of the NC thereof becomes larger. In step S48, among these feature parameters, that which has the value of the NC thereof nearest to NCb is adopted.

When the feature parameter set to be evaluated is updated by executing "the addition of a feature parameter" or/and "the adjustment of the resolution of a feature parameter", as described above, the flow returns to step S4, where the evaluation of the balance of NC in the feature parameter set thus updated is carried out. The processing (search processing of a suitable feature parameter set) in these steps S4 and S5 is repeated until it is determined that the balance of NC is good. In the above-mentioned feature parameter addition processing, a feature parameter suitable to improve the uniformity of the NC histogram is selected as an object to be added, so there is the advantage that an increase in efficiency of the search processing can be attained, and a suitable feature parameter candidate can be determined in a quicker manner. On the other hand, in the adjustment processing of the resolution of a feature parameter, it is possible to raise the uniformity of the frequency distribution by making smaller or larger the index value of a feature parameter corresponding to a portion of a maximum frequency in the NC histogram. This technique is effective in case where the NCs of feature parameters stored in the feature parameter database 11 are unevenly distributed, or in case where a feature parameter with an NC corresponding to a portion with a small frequency in the NC histogram does not exist in the feature parameter database 11, or in the like cases. Here, note that these functions of the feature parameter candidate generation part 10 correspond to the evaluation object selection unit of the present invention.

If a feature parameter set with good balance of NC is obtained in this way, the feature parameter candidate generation part 10 determines the feature parameter set as feature parameter candidates which are given to the model generation device 2 (step S6). The feature parameter candidates thus determined include feature parameters with their NCs exhaustively ranging from large to small values in a well-balanced manner, and hence it can be expected that highly reliable modeling is made possible in the later feature parameter selection processing and in the later modeling processing.

(Model Generation Device: Selection of Feature Parameters and Modeling)

In step S7, the model preparation part 20 creates or generates model candidates (candidates for an estimate equation). Here, the model preparation part 20 creates model candidates for all combinations of feature parameters included in the feature parameter candidates. However, in cases where there are too many feature parameters and it is not realistic to evaluate all the combinations thereof, the number of model candidates may be limited in a suitable manner such as by fixing the number of feature parameters to be selected. (For example, assuming that the total number of feature parameters is n and the number of feature parameters to be selected is m, then the number of model candidates will be limited to nCm.)

As the models, there are linear models such as a single regression model, a multiple regression model, etc., and nonlinear models such as a neural network, an SVM, etc., and any of such models may be used. In addition, the model preparation part 20 may change the form of models to be used adaptively in accordance with the kind, the number, etc., of feature parameters which are included in given feature parameter candidates, or may create a plurality of forms model candidates for one set of feature parameters.

In step S8, the model preparation part 20 reads the value of each of the feature parameters from the feature parameter database 11, and learns the coefficient of each model candidate. As learning techniques, there are a method of least squares, a back propagation method, and so on, and an optimal learning technique may be selected according to the form of a model candidate.

Subsequently, the processing of narrowing down an optimal feature parameter and an optimal model out of a plurality of model candidates obtained in steps S7 and S8 is carried out. Here, an index of AIC (Akaike Information Criterion) is used for selection of feature parameters and a model. The AIC is a statistical criterion for selecting a model which is compatible with model simplicity and the compatibility performance to known data. In step S9, the feature parameter and model selection part 21 calculates AIC for each model candidate. Then, in step S10, a model candidate with the smallest AIC is selected as an optimal model, i.e., a model which is compatible with simplicity and compatibility performance to known data. Here, note that as an index for evaluating a feature parameter and a model, there can be used not only AIC but also other indices such as a Cp value, etc.

Thereafter, in step S11, the model evaluation part 22 evaluates the performance of a selected model. Specifically, an estimation error of the model is calculated by the use of sample data for verification, and it is determined whether the model is adopted, based on whether the estimated error is within an allowable range. In cases where an estimation error exceeds the allowable range, models may be sequentially evaluated in an increasing order from the second smallest value of AIC. In cases where a model which satisfies a performance target is not still found, feature parameter candidates may be re-created or updated (steps S3-S6), or model candidates may be re-created (steps S7, S8).

As stated above, in the technique of this embodiment, the property of each feature parameter is quantified by a normalization cardinality. Then, candidates of feature parameters are selected so that the frequency distribution of the index values NC thereof may become uniform to a certain extent. By doing so, feature parameters of various properties will be exhaustively arranged in a well-balanced manner as feature parameter candidates. Then, by performing modeling based on such feature parameter candidates, it can be expected to improve the accuracy and stability of a model.

Example

Evaluation Experiment

In order to verify the validity of selecting a feature parameter in consideration of its normalization cardinality NC, three models (estimate equations) in which the tendencies in NC of adopted feature parameters are different from one another were prepared, and the estimation accuracy and stability of each model were evaluated.

1. Estimate Equations

The estimate equations thus prepared are as follows. Here, note that these estimate equations are models for estimating a visceral fat area based on feature parameters measured or acquired from a human. The meaning of each of the feature parameters is omitted.

(Method 1)

A method 1 is an estimate equation that has been proposed in earlier studies. In the following equation, "NC(x)" indicates the value of the NC of a feature parameter x.

$$VFA = \alpha w^2 - \beta \frac{1}{Z} - \gamma Xw - \delta \alpha, \beta, \gamma, \quad \text{[Equation 1]}$$

$$\delta : \text{regression coefficients } w^2, \frac{1}{Z},$$

$$Xw : \text{feature parameters}$$

$$NC(1/Z) = NC(Xw) = 1.00, NC(w^2) = 0.72$$

(Method 2)

A method 2 is an estimate equation built by the modeling system of the above-mentioned embodiment. The following equation exhaustively includes feature parameters with their NCs ranging from a large value to a small value.

$$VFA = \alpha_1 a + \alpha_2 b + \alpha_3 \frac{1}{b} + \alpha_4 a^2 + \alpha_5 b^2 + \quad \text{[Equation 2]}$$

$$\alpha_6 \frac{1}{b^2} + \alpha_7 \frac{1}{Z} + \alpha_8 X\sqrt{a^2+b^2} + \alpha_9 A + \alpha_{10} S +$$

$$\alpha_{11} \alpha_i (i = 1, 2, \ldots, 11) : \text{regression coefficients } a,$$

$$b, \frac{1}{b}, a^2, b^2, \frac{1}{b^2}, \frac{1}{Z}, X\sqrt{a^2+b^2},$$

$$A, S : \text{feature parameters}$$

$$NC(1/Z) = NC(X\sqrt{a^2+b^2}) = 1.00$$

$$NC(b) = NC(1/b) = NC(b^2) = NC(1/b^2) = 0.98$$

$$NC(a) = NC(a^2) = 0.80$$

$$NC(A) = 0.40, NC(S) = 0.02$$

(Method 3)

A method 3 is an estimate equation that is obtained by removing feature parameters A, S of small NCs from the estimate equation of the method 2. That is, the method 3 is the estimate equation composed of only feature parameters of large NCs.

$$VFA = \beta_1 a + \beta_2 b + \beta_3 \frac{1}{b} + \beta_4 a^2 + \beta_5 b^2 + \beta_6 \frac{1}{b^2} + \quad \text{[Equation 3]}$$

$$\beta_7 \frac{1}{Z} + \beta_8 X\sqrt{a^2+b^2} + \beta_9 \beta_i (i = 1, 2, \ldots, 9):$$

$$\text{regression coefficients } a, b, \frac{1}{b}, a^2, b^2, \frac{1}{b^2}, \frac{1}{Z},$$

$$X\sqrt{a^2+b^2} : \text{feature parameters}$$

$$NC(1/Z) = NC(X\sqrt{a^2+b^2}) = 1.00$$

$$NC(b) = NC(1/b) = NC(b^2) = NC(1/b^2) = 0.98$$

$$NC(a) = NC(a^2) = 0.80$$

2. Evaluation Indices

In this evaluation experiment, a coefficient of correlation and an error standard deviation are used as indices for evaluating the high estimation accuracy and stability of each estimate equation. In addition, a standard deviation of a regression coefficient is used as an index for evaluating the stability of each estimate equation. The details of these evaluation indices are shown below.

(Coefficient of Correlation)

An evaluation is made as to whether the expression performance to an unknown individual, i.e., high estimation accuracy with respect to individuals having visceral fat areas ranging from a small value to a large value, can be ensured by calculating the correlation between an estimated value of a visceral fat area obtained according to an arbitrary estimate equation and a true value thereof obtained from MRI by the use of Pearson's product moment correlation coefficient.

(Error Standard Deviation)

The stability of the estimation accuracy to an unknown individual is evaluated by means of the standard deviation of an error (hereinafter referred to as an error SD) between an estimated value by an arbitrary estimate equation and an actual measurement obtained from MRI.

(Standard Deviation of Regression Coefficient)

A plurality of learning data sets are prepared, and the stability of an estimate equation to individual differences in learning data is evaluated by the standard deviation of a regression coefficient at the time when the regression coefficient of an arbitrary estimate equation has been learned.

3. Experimental Method

In performing a comparative evaluation of the methods 1, 2 and 3, a cross validation is carried out. Hereinafter, the procedure thereof will be shown.

(1) in order to create a learning data group and a verification data group, data of a subject (persons to be tested) group stored in the feature parameter database 11 is divided into two groups at random. Here, note that in this experiment, the number of individuals of the learning data group and the number of individuals of the verification data group were made the same.

(2) The regression coefficient of each estimate equation is learned for one of the data groups.

(3) An estimated value is calculated from each estimation equation by the use of the other data group.

(4) A coefficient of correlation between each estimated value and a measured value by MRI is calculated, and an error SD therebetween is also calculated.

(5) In order to verify the stability of each estimate equation, the above-mentioned processes (1)-(4) are carried out a plurality of times. In this experiment, the number of times of execution was set to 10.

4. Evaluation Result

Figure 8:
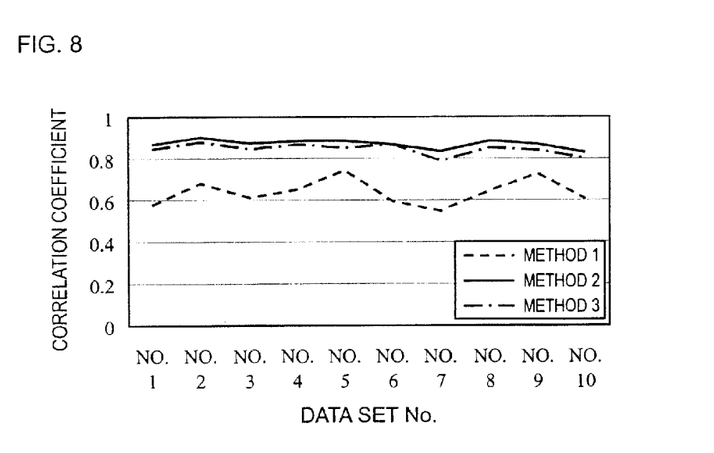
FIG. 8 is a view showing the changes over time of coefficients of correlation.
Figure 9:
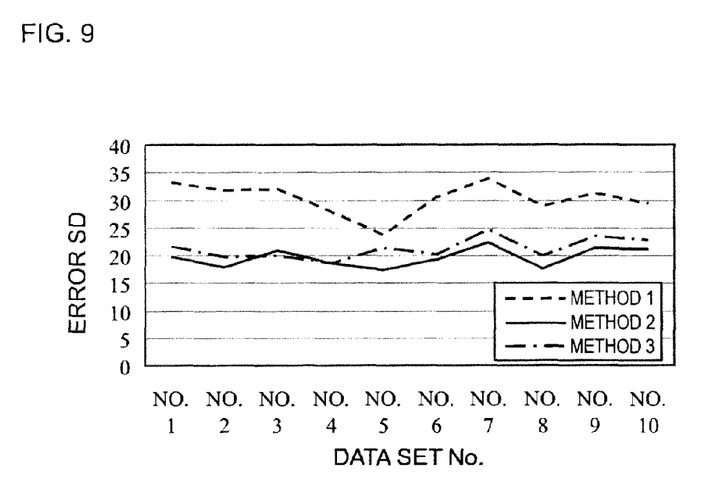
FIG. 9 is a view showing the changes over time of error SDs.

The changes over time of the coefficients of correlation between an estimated value and a measured value according to the respective methods in ten trials is shown in FIG. 8, and the changes over time of the error SDs therebetween according to the respective methods in ten trials are shown in FIG. 9.

From FIG. 8, it can be seen that the expression performance of the visceral fat area according to the method 2 and the method 3 became higher than that according to the system 1 which is a conventional method. In addition, from FIG. 9, it has been verified that the same is true of the stability of the estimation accuracy with respect to an unknown living body.

Here, the method 2 and the method 3 include a lot of feature parameters with large NCs as compared with the method 1. That is, it has been verified that the estimation accuracy is improved by introducing feature parameters with large NCs into estimate equations.

Figure 10:
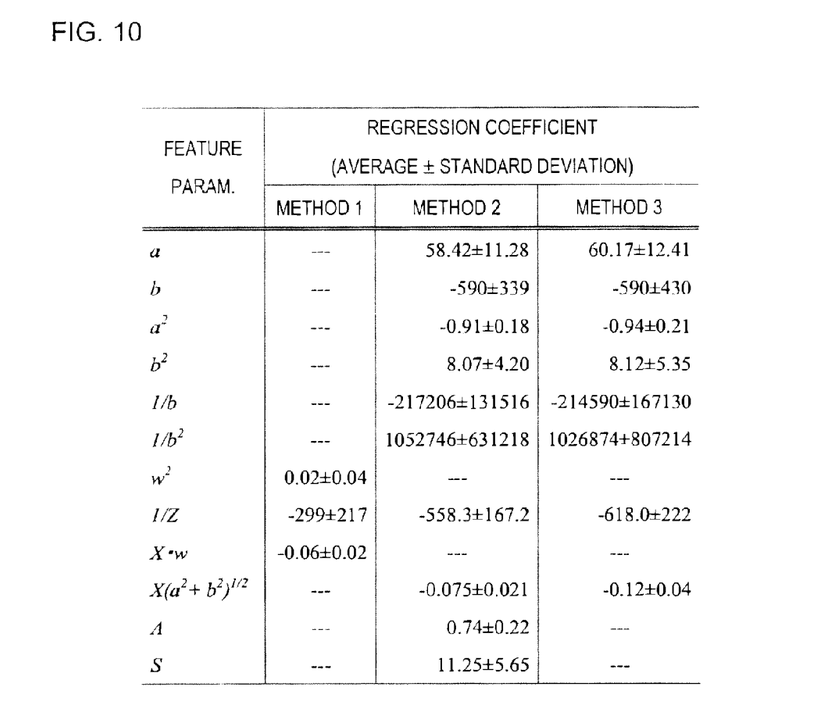
FIG. 10 is a table showing averages and standard deviations of regression coefficients for each method.

In addition, FIG. 10 shows averages and standard deviations of regression coefficients corresponding to individual feature parameters of individual estimate equations, respectively, obtained in ten trials performed in evaluation experiments. In FIG. 10, when a comparison is made between the standard deviations of regression coefficients for feature parameters included in common in the method 2 and the method 3, the standard deviation of each regression coefficient of the method 2 is smaller by 9 to 48% than that of the method 3. As a result, it can be said that the method 2 can build an estimate equation in a more stable manner as compared with the method 3. That is, it has been verified that the stability of an estimate equation is improved by introducing feature parameters with small NCs into the estimate equation.

From the above result, it can be seen that a highly precise estimate equation can be built in a stable manner by preparing and selecting a feature parameter with the use of the technique of this embodiment.

The invention claimed is:

1. A feature parameter candidate generation apparatus for generating feature parameter candidates to be given to a model generation device that builds a model by using a plurality of feature parameters selected from given feature parameter candidates, the apparatus comprising one or more computers; and
    a storage unit that stores the values of a plurality of kinds of feature parameters extracted from each of a plurality of samples;
    wherein the one or more computers are configured with:
    an index value calculation unit that calculates an index value, which is obtained by normalizing the number of the kinds of the values of the feature parameter by the number of the samples, for each feature parameter of the plurality of kinds of feature parameters;
    an evaluation object selection unit that selects a subset of feature parameters out of the plurality of kinds of feature parameters;
    an evaluation unit that judges whether the subset of feature parameters selected by the evaluation object selection unit has a desired balance of the index values, by evaluating whether the uniformity of a frequency distribution of the index values satisfies a predetermined criterion; and
    a candidate determination unit that determines the subset of feature parameters as feature parameter candidates to be given to the model generation device, when the subset of feature parameters is judged to have the desired balance of the index values by the evaluation unit.

2. The feature parameter candidate generation apparatus as set forth in claim 1, wherein;
    an update of a subset of feature parameters by the evaluation object selection unit and an evaluation of the updated subset of feature parameters by the evaluation unit are repeated so as to find out a subset of feature parameters which has a desired balance of index values.

3. The feature parameter candidate generation apparatus as set forth in claim 2, wherein;
    the evaluation object selection unit updates the subset of feature parameters by adding, among the plurality of kinds of feature parameters, a feature parameter which is not included in the subset of feature parameters to the subset of feature parameters; and
    the evaluation object selection unit specifies a portion which indicates a minimum frequency in a frequency distribution of index values of feature parameters included in the subset of feature parameters, and selects, as a feature parameter added to the subset of feature parameters, a feature parameter which has an index value corresponding to the portion indicating the minimum frequency.

4. The feature parameter candidate generation apparatus as set forth in claim 3, wherein;
    the evaluation object selection unit updates the subset of feature parameters by changing resolution of the values of at least any feature parameter among feature parameters included in the subset of feature parameters; and
    the evaluation object selection unit specifies a portion which indicates a maximum frequency in a frequency distribution of index values of feature parameters included in the subset of feature parameters, and changes the resolution of a feature parameter which has an index value corresponding to the portion indicating the maximum frequency.

5. The feature parameter candidate generation apparatus as set forth in claim 2 wherein;
    the evaluation object selection unit updates the subset of feature parameters by changing resolution of the values of at least any feature parameter among feature parameters included in the subset of feature parameters; and
    the evaluation object selection unit specifies a portion which indicates a maximum frequency in a frequency distribution of index values of feature parameters included in the subset of feature parameters, and changes the resolution of a feature parameter which has an index value corresponding to the portion indicating the maximum frequency.

6. A feature parameter candidate generation method for generating feature parameter candidates to be given to a model generation device that builds a model by using a plurality of feature parameters selected from given feature parameter candidates, the method wherein;
    a computer, which is provided with a storage unit that stores the values of a plurality of kinds of feature parameters extracted from each of a plurality of samples, executes:
    an index value calculation step that calculates an index value, which is obtained by normalizing the number of the kinds of the values of the feature parameter by the number of the samples, for each feature parameter of the plurality of kinds of feature parameters;
    an evaluation object selection step that selects a subset of feature parameters out of the plurality of kinds of feature parameters;

an evaluation step that judges whether the subset of feature parameters selected by the evaluation object selection step has a desired balance of the index values, by evaluating whether uniformity of a frequency distribution of the index values satisfies a predetermined criterion; and
a candidate determination step that determines the subset of feature parameters as feature parameter candidates to be given to the model generation device, when the subset of feature parameters is judged to have the desired balance of the index values by the evaluation step.

7. A non-transitory computer readable storage medium storing a feature parameter candidate generation program for generating feature parameter candidates to be given to a model generation device that builds a model by using a plurality of feature parameters selected from given feature parameter candidates, the program characterized by causing a computer, which is provided with a storage unit that stores the values of a plurality of kinds of feature parameters extracted from each of a plurality of samples, to execute:

an index value calculation step that calculates an index value, which is obtained by normalizing the number of the kinds of the values of the feature parameter by the number of the samples, for each feature parameters of the plurality of kinds of feature parameters;
an evaluation object selection step that selects a subset of feature parameters out of the plurality of kinds of feature parameters;
an evaluation step that judges whether the subset of feature parameters selected by the evaluation object selection step has a desired balance of the index values, by evaluating whether uniformity of a frequency distribution of the index values satisfies a predetermined criterion; and
a candidate determination step that determines the subset of feature parameters as feature parameter candidates to be given to the model generation device, when the subset of feature parameters is judged to have the desired balance of the index values by the evaluation step.

* * * * *